United States Patent [19]
Wang

[11] Patent Number: 5,325,730
[45] Date of Patent: Jul. 5, 1994

[54] THIN FILM SAMPLER FOR FILM COMPOSITION QUANTITATIVE ANALYSIS

[75] Inventor: Wonder D. Wang, Taipei, Taiwan

[73] Assignee: Taiwan Semiconductor Manufacturing Company, Hsinchu, Taiwan

[21] Appl. No.: 84,941

[22] Filed: Jul. 1, 1993

Related U.S. Application Data

[62] Division of Ser. No. 758,564, Sep. 12, 1991, Pat. No. 5,248,614.

[51] Int. Cl.⁵ ............... H01L 21/66; H01L 21/306; G01N 31/00; G01N 1/28
[52] U.S. Cl. ............................................ 73/863; 437/8
[58] Field of Search ............... 73/864.91, 863, 863.21, 73/863.31, 863.32, 800; 422/292, 293, 297, 300, 301, 68.1, 101, 104; 436/2–6, 174–181; 324/158 F; 156/378, 379, 626, 627; 437/8, 225, 228; 29/705

[56] References Cited

U.S. PATENT DOCUMENTS

| | | | |
|---|---|---|---|
| 1,792,606 | 2/1931 | Richards et al. | 156/626 X |
| 2,959,471 | 11/1960 | Morgia | 73/104 X |
| 4,244,775 | 1/1981 | D'Asaro | 156/345 X |
| 4,512,847 | 4/1985 | Brunsch et al. | 156/626 |
| 4,544,446 | 10/1985 | Cady | 156/639 |
| 4,551,434 | 11/1985 | Thoma | 73/104 X |
| 4,584,886 | 4/1986 | Matsunaga et al. | 73/863 |
| 4,634,497 | 1/1987 | Shimazaki | 156/646 |
| 4,783,172 | 11/1988 | Garg | 73/864.51 X |
| 4,885,941 | 12/1989 | Vardoulakis et al. | 73/819 X |
| 4,996,160 | 2/1991 | Hazlitt et al. | 324/71.1 |
| 5,264,184 | 11/1993 | Aysta et al. | 422/101 |

FOREIGN PATENT DOCUMENTS

| | | | |
|---|---|---|---|
| 75639 | 4/1988 | Japan | 73/863.21 |
| 312259 | 12/1990 | Japan | 156/379 |
| 188642 | 8/1991 | Japan | 156/626 |
| 189536 | 8/1991 | Japan | 73/864.91 |
| 197838 | 8/1991 | Japan | 73/864.91 |

OTHER PUBLICATIONS

"VLSI Technology" Second Edition by S. M. Sze, Published by McGraw Hill International Editions, N.Y., N.Y., 1988, Chapter 12.4 pp.548–554.

*Primary Examiner*—Thomas P. Noland
*Attorney, Agent, or Firm*—George O. Saile

[57] ABSTRACT

A semiconductor test fixture is described for sampling thin films on the surface of a semiconductor wafer in the process of manufacturing integrated circuits thereon. A first plate is provided for supporting the wafer. At least one test fluid reservoir, and usually three reservoirs having a projecting collar or flange around one end thereof an an O-ring under the collar. A second late having at least one opening therein for allowing the major portion of the at least one test fluid reservoir to pass through and with the collar of the reservoir supporting the second plate. A hand screw is associated with the first and second plates for tightening second plate against the collar of the reservoir and, in turn the O-ring of the collar against the wafer which is supported upon the first plate so as to allow a fluid to be contained in the reservoir without leakage.

5 Claims, 1 Drawing Sheet

THIN FILM SAMPLER FOR FILM COMPOSITION QUANTITATIVE ANALYSIS

This is a division of U.S. application Ser. No. 07/758,564 filed Sep. 12, 1991 and now U.S. Pat. No. 5,248,614.

BACKGROUND OF THE INVENTION

(1) Field Of The Invention

This invention relates to a semiconductor wafer test fixture and to methods for analyzing ultratrace amount of impurities in thin films present on the surface of the semiconductor wafer.

(2) Description Of The Prior Art

The present means of chemically analyzing the chemical composition of thin films is destructive to the semiconductor wafer on which the thin films are located. A fixed area die is cut from the wafer, the thin films on the die is etched and this liquid transferred with extreme care to another vessel. The fluid is diluted and then the chemical nature of the thin film is determined with a chromatograph.

The book entitled "VLSI TECHNOLOGY" Second Edition by S. M. Sze Published by McGraw-Hill International Editions, New York, NY., 1988 in its Chapter 12.4 pages 548–554 describes the use of chromatography and preparation of samples therefor. The U.S. Pat. No. 4,854,886 describes a method where silicon oxide or nitride films on wafers are dissolved with hydrofluoric acid and the solution collected and then sent to be checked for impurities in atomic absorption spectrophotometer. Other patents U.S. Pat. No. 3,976,377 and U.S. Pat. No. 3,824,016 describe other testing methods for semiconductor wafers. None of these publications provide accurate, fast, and safe methods or fixtures that allow wafer to be reused, i.e., that there is no requirement for dicing of the wafer.

SUMMARY OF THE INVENTION

A principal object of the invention is to provide a semiconductor film test fixture which is capable of preparing semiconductor film samples for ion testing wherein transfer loss and dilution error are avoided.

Another object of this invention is to provide a semiconductor film test fixture and method which is capable of preparing semiconductor film samples which is non-destructive of the wafer.

Another object of this invention is to provide a semiconductor film test fixture and method which is capable of preparing semiconductor film samples which is safe for any operator.

Another object of the invention is to provide a semiconductor film test method that allows for the possibility of wafer thickness correlation.

These objects of this invention are accomplished by a method for analyzing ultratrace amounts of impurities in thin films present on semiconductor wafers without destroying the semiconductor wafer. The wafer having thin films to be analyzed is positioned into a testing device or fixture having at least one fluid reservoir. The testing device is tightened and sealed to the wafer so that the fluid reservoir is open to the thin films on the wafer, but otherwise sealed to the ambient. A reagent fluid is provided in the reservoir which dissolves the thin films on the wafer and allowing sufficient time for the fluid to dissolve the thin films. A diluent is added to the reservoir and the fluids are mixed. The mixed fluids are sampled and analyzed to determine the chemical nature of the thin films on the wafer. Samples are removed from the test fluid reservoirs to be tested as in an ion chromatograph, after the quantitative test, the wafer can be tested for weight difference and thin film edge step height by analytical balance (+or −0.01 mg.) and step height measurement, such as alpha step or Dektak which can be correlated.

A semiconductor test fixture is also provided for sampling thin films on the surface of a semiconductor wafer in the process of manufacturing integrated circuits thereon. A first plate is provided for supporting the wafer. At least one test fluid reservoir, and usually three reservoirs, each having a bottom opening, a projecting collar or flange around one end thereof and an annular sealing means under the collar surrounding the opening. A second plate having at least one test fluid reservoir to pass through and with the collar of the reservoir supporting the second plate. Means are associated with the first and second plates for tightening the second plate against the collar of the reservoir and, in turn the sealing means of the collar against the wafer which is supported upon the first plate so as to allow a fluid to be contained in the reservoir without leakage.

BRIEF DESCRIPTION OF THE DRAWINGS

In the accompanying drawings and preferred embodiment of this device, there is shown.

DESCRIPTION OF THE PREFERRED EMBODIMENTS

Figure 1:
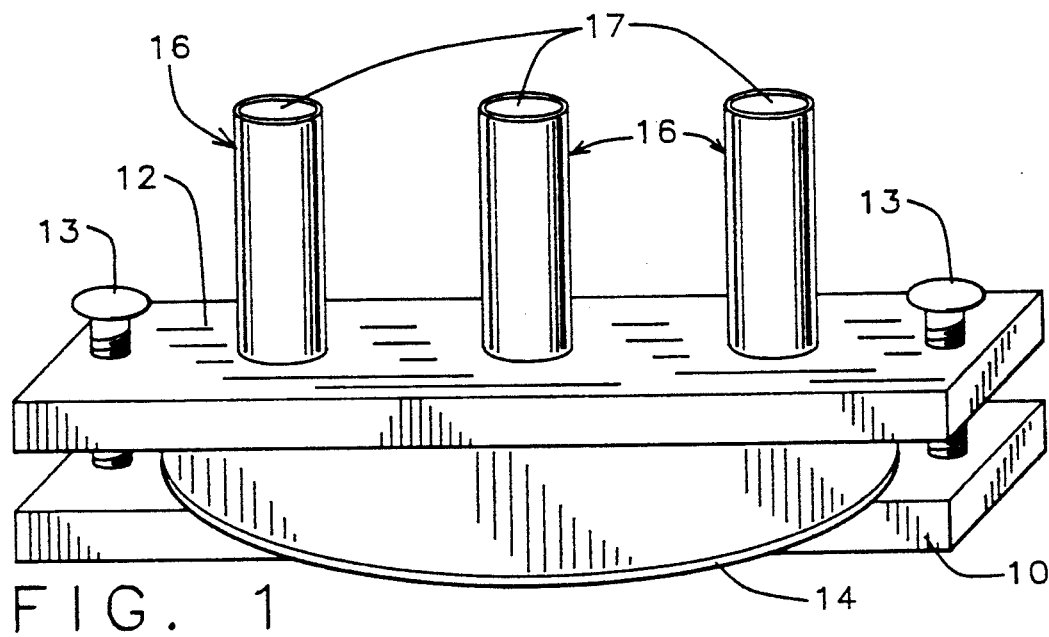
FIG. 1 is a full view of an embodiment of the test fixture for sampling and analyzing semiconductor thin films in accordance-with the present invention.
Figure 2:
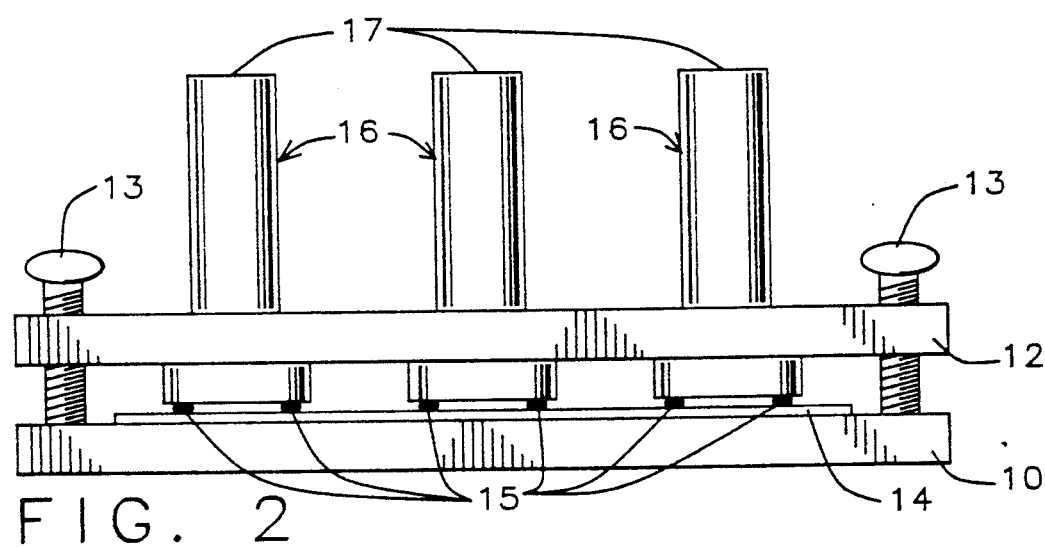
FIG. 2 is a side view of the FIG. 1 embodiment of the test fixture for semiconductor thin films in accordance with the present invention.
Figure 3:
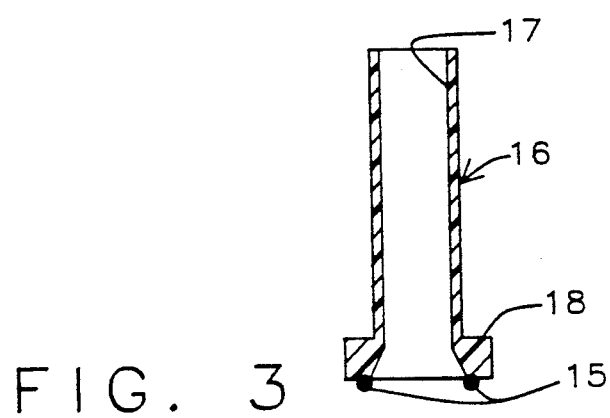
FIG. 3 is a cross-sectional view of a single test fluid reservoir for the FIG. 1 embodiment of the test fixture for semiconductor films in accordance with the present invention.

Referring now more particularly to FIG. 1, there is shown a test fixture or device for sampling thin films present upon semiconductor wafers embodying the present invention. This semiconductor film test fixture device includes first base plate 10 and second upper plate 12. These plates must be strong, so they are preferably made of a metal, such as steel. The first plate 10 supports the wafer 14 having thin films thereon to be analyzed. At least one test fluid reservoir 16, and usually three reservoirs, each having a bottom opening an annular flat surface surrounding the opening, a projecting collar or flange 18 around one end thereof and a sealing means, preferably a O-ring structure 15 under the collar 18 in contact with the annular surface surrounding the openings, as seen in FIG. 3. The major cylindrical portion 17 of the reservoir is typically made of plastic material such as high density polyethylene.

The diameter of the cylindrical portion can be between about 5 to 150 millimeters. Where it is desired to test, for example the contamination on one whole side of a wafer's surface, the cylindrical portion can be substantially the whole wafer diameter, such as 150 millimeters. It is sometimes considered that there are statistical difficulties encountered when only Some sites of the wafer are tested. Contamination can thereby be tested on the front and back side by using a full wafer cylindrical portion of the reservoir. This helps in differentiating the contamination source. Alternatively, the cylindrical portion can be small as 5 millimeters. In this case, 3 or many more reservoirs can be used to sample the condition of the wafer's surface for mapping the whole wafer or portions thereof for obtaining localized and distributed data. This alternative may be adequate where looking for the distribution of material conditions across the wafer.

The second plate 12 has at least one opening therein for allowing the major portion 17, which is preferably cylindrical or tubular of the at least one test fluid reservoir 16 to pass through and with the collar 18 of the reservoir supporting the second plate. Means, such as hand screws 13 are associated with the first and second plates 10 and 12 for tightening second plate 12 against the collar 18 of the reservoir 16 and, in turn the sealing means 15 of the collar 18 against the wafer 14 which is supported upon the first plate 10 so as to allow a fluid to be contained in the reservoir 16 without leakage. The collar or flange 18 provides a bearing surface for O-rings 15 and prevents the test fluid reservoirs from sliding out of the metal clamping plate 12.

Next the method of using the test fixture or device for sampling for composition analysis will be described. The wafer to be tested is inserted into the resolution device and secured as described above. A reagent fluid is added to the reservoir or reservoirs 16. The etching reagent is dependent on the particular material to be sampled. For example, wherein the layer to be dissolved is borophosphosilicate glass, and the chromatograph will test for boron and phosphorus, the etching or dissolving reagent will be hydrofluoric acid (15%) and the diluent is water. Other materials to be tested could be residual chloride and bromide after metal dry etching, copper in aluminum/silicon/copper metallurgy, tungsten in a titanium and tungsten metallurgy, other inorganics and organic materials such as resists, and spin-on-glass materials. The etchant or reagent for copper in aluminum/silicon/copper can be KOH and HF. The reagent for titanium/tungsten can be $NH_4OH:H_eO_e:H_eO = 1:1:1$ ratio and any suitable diluent. The reagent for chlorides is water and the diluent is water. The reagent for organic materials is acetone or methyl isobutyl ketone and the diluent fluid can be any suitable fluid. The reagent is hydrofluoric acid (15%) for cured spin-on-glass and the diluent may be water. After the diluent is added the fluids are mixed for 5 to 10 seconds by bubble method. Other methods of agitation are possible and can include stirring shaking and the like.

The reagent fluid dissolves the thin film layers on the semiconductor wafer in the sampling device. A diluent, such as water, is added to the reservoirs 16 and bubbled with a small diameter tube for 5 to 10 seconds to mix.

Ion chromatograph samples are removed from the reservoirs with a plastic tube using suction and the samples taken to the ion chromatograph or graphite furnace atomic absorption spectrometer for analysis.

Resolution by the present method achieves a high degree of accuracy because the wafer can be tested within the manufacturing area thereby decreasing transfer loss and dilution errors. The present method has only a few, simple steps that are safe for the operator to perform. By using three test fluid reservoirs and sampling three times in different places, nine points of data can be collected for one six-inch wafer, allowing composition uniformity to be attained.

While the invention has been particularly shown and described with reference to the preferred embodiments thereof, it will be understood by those skilled in the art that various changes in form and details may be made without departing from the spirit and scope of the invention.

What is claimed is:

1. A semiconductor test fixture for sampling thin films on the surface of a semiconductor wafer in the process of manufacturing integrated circuits thereon comprising:
    a first plate for supporting said wafer;
    at least one test fluid reservoir having a projecting collar around one end thereof and a sealing means under said collar;
    a second plate having at least one opening therein for allowing the major portion of said at least one test fluid reservoir to pass through and with said collar of the reservoir supporting said second plate;
    means associated with said first and second plates for tightening said second plate against said collar of the reservoir and in turn the sealing means of said collar against said wafer which is supported upon said first plate so as to allow a fluid to be contained in said reservoir without leakage.

2. The test fixture of claim 12 wherein said at least one reservoir is substantially cylindrical and said sealing means is an O-ring.

3. The test fixture of claim 2 wherein there are at least three of said at least one reservoir composed of plastic tubular material and said first and second plates are composed of steel.

4. The test fixture of claim 3 wherein said plastic tubular reservoirs have diameters of between about 5 to 150 millimeters.

5. The test fixture of claim 3 wherein said means for tightening include a hand screw which coacts with said first and second plates.

* * * * *